United States Patent
Park et al.

(10) Patent No.: US 6,957,097 B2
(45) Date of Patent: Oct. 18, 2005

(54) RAPID MEASUREMENT OF TIME-AVERAGED BLOOD FLOW USING UNGATED SPIRAL PHASE-CONTRAST MRI

(75) Inventors: Jong B. Park, Mountain View, CA (US); Dwight B. Nishimura, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 547 days.

(21) Appl. No.: 10/125,010

(22) Filed: Apr. 17, 2002

(65) Prior Publication Data

US 2003/0199750 A1 Oct. 23, 2003

(51) Int. Cl.[7] ................................. A61B 5/05
(52) U.S. Cl. ...................... 600/419; 419/410
(58) Field of Search ................. 600/419, 410, 600/411, 412, 413, 414, 415, 416, 417, 418; 324/386, 307, 308, 309

(56) References Cited

U.S. PATENT DOCUMENTS

| | | | |
|---|---|---|---|
| 4,528,985 A | | 7/1985 | Macovski |
| 4,595,879 A | | 6/1986 | Lent et al. |
| 4,609,872 A | | 9/1986 | O'Donnell |
| 4,683,431 A | | 7/1987 | Pattany et al. |
| 4,718,424 A | | 1/1988 | Nishimura |
| 5,877,629 A | * | 3/1999 | King et al. ................. 324/309 |
| 6,518,759 B2 | * | 2/2003 | Bernstein ................... 324/307 |
| 6,630,828 B1 | * | 10/2003 | Mistretta et al. ............ 324/309 |
| 6,671,541 B2 | * | 12/2003 | Bishop et al. .............. 600/436 |

OTHER PUBLICATIONS

Hangiandreau, N.J. et al., "Analysis of MR Phase–Contrast Measurements of Pulsatile Velocity Waveforms," J. Magn Reson Imaging, 3:387–394, 1993.

Hofman Mark B.M. et al., "Nontriggered Magnetic Resonance Velocity Measurement of the Time–Average of Pulsatile Velocity," Magn Reson Med, 29:648–655, 1993.

Jordan J.E. et al., "Velocity and Flow Quantitation in the Superior Sagittal Sinus with Ungated and Cine (Gated) Phase–Contrast MR Imaging," J Magn Reson Imaging, 4:25–28, 1994.

Bakker, C.J.G. et al., "Measuring Blood Flow by Nontriggered 2D Phase–Contrast MR Angiography," Magn Reson Imaging, 14:609–614, 1996.

Bakker, C.J.G. et al., "Construction of a Protocol for Measuring Blood Flow by Two–Dimensional Phase–Contrast MRA," J Magn Reson Imaging, 9:119–127 (1999).

* cited by examiner

*Primary Examiner*—Daniel Robinson
(74) *Attorney, Agent, or Firm*—Beyer Weaver & Thomas LLP (57) ABSTRACT

Pulsatile flow is measured using magnetic resonance imaging without cardiac gating using a phase-contrast excitation method to rapidly quantify blood flow and using a spiral k-space trajectory for image data read-out to mitigate deleterious effects of pulsatility. Post-processing of the read-out data provides a cumulative-average velocity plot from which a period of a cardiac cycle is obtained. Time-averaged blood flow rates can be rapidly and robustly measured and is more repeatable than conventional gated techniques.

18 Claims, 7 Drawing Sheets

RAPID MEASUREMENT OF TIME-AVERAGED BLOOD FLOW USING UNGATED SPIRAL PHASE-CONTRAST MRI

BACKGROUND OF THE INVENTION

This invention relates to the use of magnetic resonance imaging (MRI) techniques, and more particularly the invention relates to the measurement of blood flow using MRI.

The knowledge of time averaged blood flow is clinically important for diagnosing various vascular-related diseases, and a quick and robust tool for measuring time-averaged blood flow is extremely needed in clinical settings. Phase-contrast (PC) MR imaging can be an accurate tool for measuring time-averaged blood flow rates, information that can be helpful for diagnosing various diseases such as portal venous or pulmonary arterial hypertension. Cardiac gated techniques, such as cine PC can be used to measure time-averaged flow rates from time-resolved data. However, the long scan times, typically several minutes, of cine PC can degrade the accuracy and repeatability due to irregular heart rhythm or respiratory motion. Faster gated methods or real time techniques can provide alternative methods in measuring time-averaged flow rates with shorter scan times. However, the low spatial resolution of these methods limits their clinical applications to relatively large vessels.

Applying a PC pulse sequence without cardiac gating could significantly reduce scan times compared to gated PC methods while achieving sufficient spatial resolution. Ungated PC methods with a two-dimensional Fourier transform (2DFT) trajectory can produce accurate measurements of time-averaged flow rates if the flow is steady or only weakly pulsatile. However, successful applications of these methods can require prior information of the imaging object (e.g., vessels size, flow waveform, and the like) careful selection of the scan perimeters, and scan times inconveniently longer than a breath hold. Moreover, if the flow is strongly pulsatile, these methods cannot repeatedly produce accurate measurements within reasonable scan times.

The present invention is directed to an MR technique for rapidly and robustly measuring time averaged flow rates even in small arteries and in the presence of strong pulsatility.

BRIEF SUMMARY OF THE INVENTION

In accordance with the invention, phase contrast (PC) imaging without cardiac gating is employed to rapidly quantify blood flow. The deleterious effects of pulsatility in the blood flow is mitigated by using spiral k-space read-out trajectories or similar k-spaced trajectories which have similar k-space sampling nature such as projection reconstruction, twisted radial lines, and variable-density spiral trajectories. The spiral trajectories sample k-space origin at every excitation. The sampling nature of spiral trajectories around the k-space origin mitigates the effects of pulsatility, and this property allows the rapid measurement of time-averaged blood flow even in small arteries and in the presence of strong pulsatility. Because temporal resolution is traded for sufficient spatial resolution, post-processing employing a cumulative-average velocity plot is employed for extracting periodic information of a cardiac cycle in order to acquire an appropriate time average.

The invention and object and features thereof will be more readily apparent from the following detailed description and dependent claims when taken with the drawings.

DETAILED DESCRIPTION OF ILLUSTRATIVE EMBODIMENTS

Figure 1:
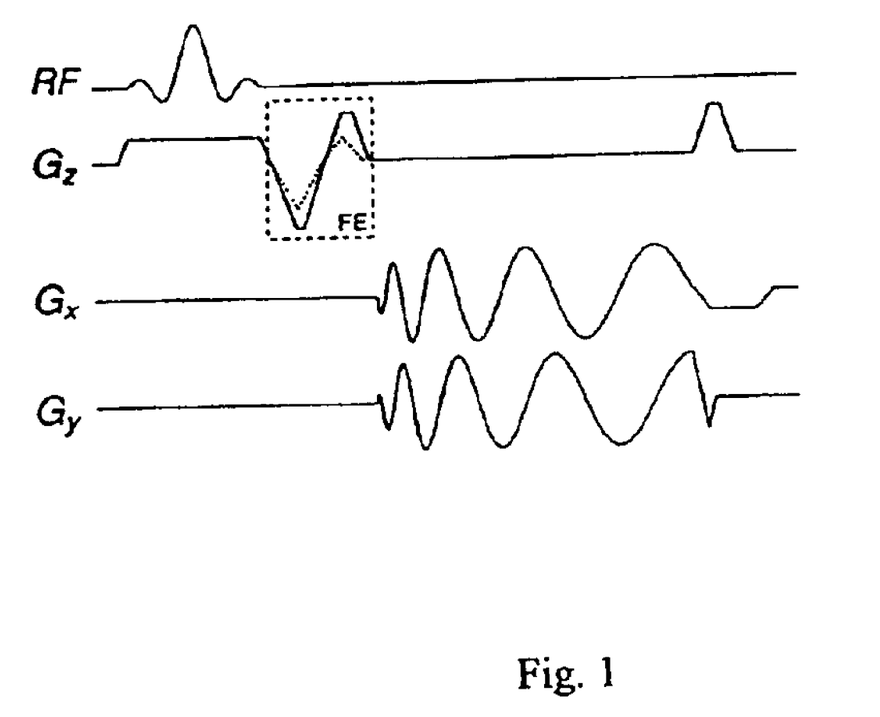
FIG. 1 illustrates an ungated spiral phase-contrast pulse sequence for use in time-averaged blood flow measurements in accordance with invention.

FIG. 1 illustrates a spiral phase-contrast (SPC) pulse sequence that can be applied in an ungated sequence as employed in an embodiment of the invention. The RF excitation pulse is applied in the presence of a $G_z$ gradient for slice selection which is followed by a flow encoding (FE) pulse which is implemented on the Z-gradient and combined with the slice select gradient lobe to minimize echo time, TE. The dotted line within the "FE" box represents an alternate FE lobe. A gradient spoiler is placed at the end of the Z-gradient, following the $G_x$ and $G_y$ read-out gradients, and the spiral waveforms are rewound after the read-out by the $G_x$ and $G_y$ gradients.

The effects of constant through-plane flow in PC methods can be understood if the spatial point-spread function (PSF) of the flow, h(x, y), in image space is examined. However, if the through-plane flow is pulsatile rather than constant and the PC pulse sequence is performed without cardiac gating, it becomes necessary to examine the Fourier Transform (FT) of the PSF in k-space, $H(k_x, k_y)$, to understand the k-space trajectory dependence of the signal from flowing spins. The PSF provides an intuitive understanding of how k-space spiral trajectories which sample k-space origin at every excitation can neutralize the effects of pulsatility.

The basis of PC imaging is the fact that spins moving in the direction of a magnetic field gradient whose first moment is non-zero cause a phase-shift of the k-space raw data relative to the k-space raw data of stationary spins. If the velocity of the moving spins is constant while a gradient with a non-zero first moment is applied, the phase offset of the moving spins will be proportional to their velocity. Therefore, the k-space raw data of an impulse (point) object with through-plane flow can be expressed simply as $$H(k_x,k_y)=\exp\{-i\gamma M_1 v_z(k_x,k_y)\} \qquad (1)$$

where $\gamma$ is the gyromagnetic ratio, $M_1$ is the first moment of the Z gradient, and $v_z(k_x,k_y)$ is the velocity of the flow at the time when the velocity is encoded by the Z gradient whose first moment, $M_1$, is non-zero in an excitation where a spiral readout samples $(k_x,k_y)$. The flow-encoding (FE) lobes in FIG. 1 are examples of such a gradient. Note that the inverse FT of H $(k_x,k_y)$ is the spatial point-spread function (PSF) of the flow, h(x,y).

Figure 2:
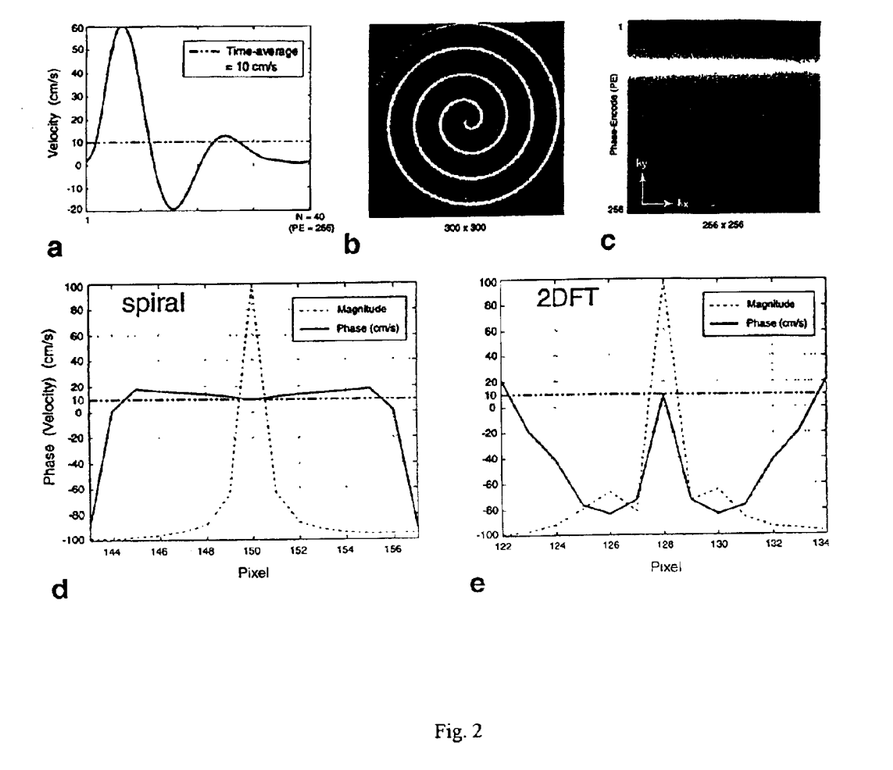
FIGS. 2A–2E illustrate simulations of spatial point-spread functions (PSF) of pulsatile flow in ungated PC sequences.

If the flow is constant, velocities throughout the scan will be constant (i.e., $v_z(k_x,k_y)=v_0$). Therefore, h(x,y) is just an impulse with phase proportional to $v_0$—a trivial case in the PC technique. However, if the flow is pulsatile and the pulse sequence is ungated, the shape of h(x,y) will depend highly on the k-space trajectory because of the k-space dependence in $v_z(k_x,k_y)$ (see Eq. [1]). Examples for spiral and 2DFT trajectories with a typical pulsatile arterial waveform, are shown in FIG. 2. These simulations show spatial point-spread functions (PSFs) of pulsatile flow in ungated PC sequences, including a typical "triphasic" velocity waveform found in normal peripheral arteries is shown in FIG. 2A. The k-space absolute-phase images for ungated spiral (FIG. 2B) and 2DFT (FIG. 2C) sequences show how the velocity waveform is sampled in k-space. Corresponding PSFs (1D-slice through x=0 line) zoomed in on their center are shown in FIG. 2D for spiral and in FIG. 2E for 2DFT sequences, where the phase in the velocity scale (VENC= 100 cm/s) is compared with the time-averaged velocity (10 cm/s) in FIG. 2A.

On the other hand, [regardless of which k-space trajectory we use,] the phase at the center of h(x,y) will exactly denote a time-averaged velocity according to the area property of the FT if we assume the temporal velocity distribution of the pulsatile flow to be symmetric about its time-average and also assume no in-flow effects; (the asymmetric case with in-flow effects will be discussed in detail shortly). Because velocities are represented as phases of complex vectors in k-space, the phase average of the complex vectors represents the time-averaged velocity. When the phases of the complex vectors are distributed symmetrically about their phase average and when the complex vectors have the same magnitude (i.e., when we assume a symmetric temporal velocity distribution and no in-flow effects), their phase average is exactly equal to the phase of the complex-vector sum. The phase of the complex-vector sum is the phase at the center of h(x,y) (by the area property of the FT). Therefore, [regardless of which k-space trajectory we use,] the phase at the center of h(x,y) will be exactly equal to the phase average, which represents the time-averaged velocity. Note that even if the distribution is asymmetric and the magnitudes are different, the phase of the complex-vector sum will still be approximately equal to the phase average, thus making the phase at the center of h(x,y) denote the time-averaged velocity, as illustrated in FIGS. 2d and 2e.

When we measure flow rates with ungated PC methods, however, the k-space trajectory is important because it determines the shape of h(x,y) around its center, which affects how h(x,y) of pixels inside a vessel interfere with each other. In the case of spiral trajectories, which sample the k-space origin at every excitation, the magnitude of h(x,y) is likely to concentrate around the center, and the phase around the center of h(x,y) is likely to vary little (FIG. 2d), which means that the phase of each pixel is constructively interfered with by PSFs of nearby pixels. Therefore, the USPC method can produce accurate time-averaged-velocity measurements of each pixel, and a vessel cross section in the magnitude image will be minimally corrupted by the interference from adjacent pixels. These effects make an accurate measurement of time-averaged flow rate (temporal and spatial velocity average multiplied by cross-sectional area) possible with the USPC method. In the case of 2DFT trajectories, conversely, the phase near the center of a PSF is likely to vary considerably (FIG. 2e), and therefore the phase of each pixel is destructively interfered with by the PSFs of nearby pixels, causing inaccurate velocity measurements. Along with relatively severe magnitude ghosting artifacts, these effects can make time-averaged flow rates measured with 2DFT trajectories inconsistent and inaccurate.

If the temporal velocity distribution of pulsatile flow is not symmetric about its time-average, and if signal magnitudes vary due to in-flow effects during an ungated scan, the phase around and at the center of h(x,y) may not exactly represent the time-averaged velocity, and the flow measurements may contain errors. In other words, the complex vectors, whose phases represent velocities in k-space, will have different magnitudes, and their phase distribution will not be symmetric about their phase average, which represents the time-averaged velocity. Therefore, the phase of the complex-vector sum, the phase at the center of h(x,y), may not exactly represent the time-averaged velocity. However, this error usually will not be larger than other possible errors in the PC technique, given the sequence parameters generally used, and will also be relatively small if the complex vectors are concentrated around their complex-vector sum. Using a minimum-first-moment FE ($M_f=\pm\Delta M_f/2$), and making the maximum encoded velocity (VENC) approximately twice as large as the peak possible velocity in a flow cycle, one can confine the phase distribution between $\pm\pi/4$, and the errors from the asymmetry and in-flow effects will be smaller than most of the possible errors in the USPC method.

The USPC pulse sequence is a modification of a conventional 2D spiral imaging sequence, as shown in FIG. 1. The minimum-first-moment FE ($M_f=\pm\Delta M_f/2$) is implemented on the Z gradient, and to minimize TE, we combine the FE gradients with the slice-select gradient. Concomitant gradient (Maxwell term) effects arising from these non-anti-symmetric FE lobes can be corrected in the post-processing stage. With this FE scheme ($M_f=\pm\Delta M_f/2$), each image (with different FE) has the same spatial PSF if both images experience exactly the same velocities. This same spatial PSF has a more benign shape (i.e., the magnitude is more concentrated and the phase is flatter around the center) than an $M_f=\pm\Delta M_f$ flow-encoded image from the standard on-off FE scheme ($M_f=\pm\Delta M_f,0$) has, because of the smaller $M_1v_z$ ($k_x,k_y$) in Eq. [1]. To further minimize swirling artifacts from the pulsatile flow, a pseudo-randomized interleave ordering is used.

The imaging parameters are N (the number of interleaves)=40, FOV/$\Delta$x/slice thickness=30 cm/1 mm/10 mm, and TR/TE/readout time/flip angle=15 ms/3.5 ms/7.4 ms/30°, and VENC=100 cm/s. The 1 mm spatial resolution ($\Delta$x) is used because the vessel (or tube) diameters of interest are 5–7 mm in our experiments. The 10 mm slice thickness is used to keep the SNR high while keeping the partial-volume effect (PVE) in the through-plane direction within a clinically tolerable range; we minimize this PVE by prescribing an oblique slice, perpendicular to the vessel of interest, from scout scans—a technique we employ routinely. The shortest possible TR (and TE) are used to achieve sufficient temporal sampling of the velocity waveform. In our experiments, we assume the peak velocities of pulsatile flow to be 30–80 cm/s, and therefore the FE gradient lobes are designed to achieve a VENC of 100 cm/s.

Since the sequence runs ungated, we alternate the FE at every excitation and change the spiral readout (interleave) at every even excitation to acquire each image set (with different FE) from the same portion of the cardiac cycle. The scan is played out five times continuously, to ensure that integer multiples of the cardiac cycle are covered.

To determine the appropriate time-averaged flow rate, we need to know the period of a cardiac cycle. If L excitations (assuming L=2k where k≧N) approximately cover integer multiples of a cardiac cycle, we can measure the time-averaged flow rate by applying the PC technique to L excitations.

Figure 3:
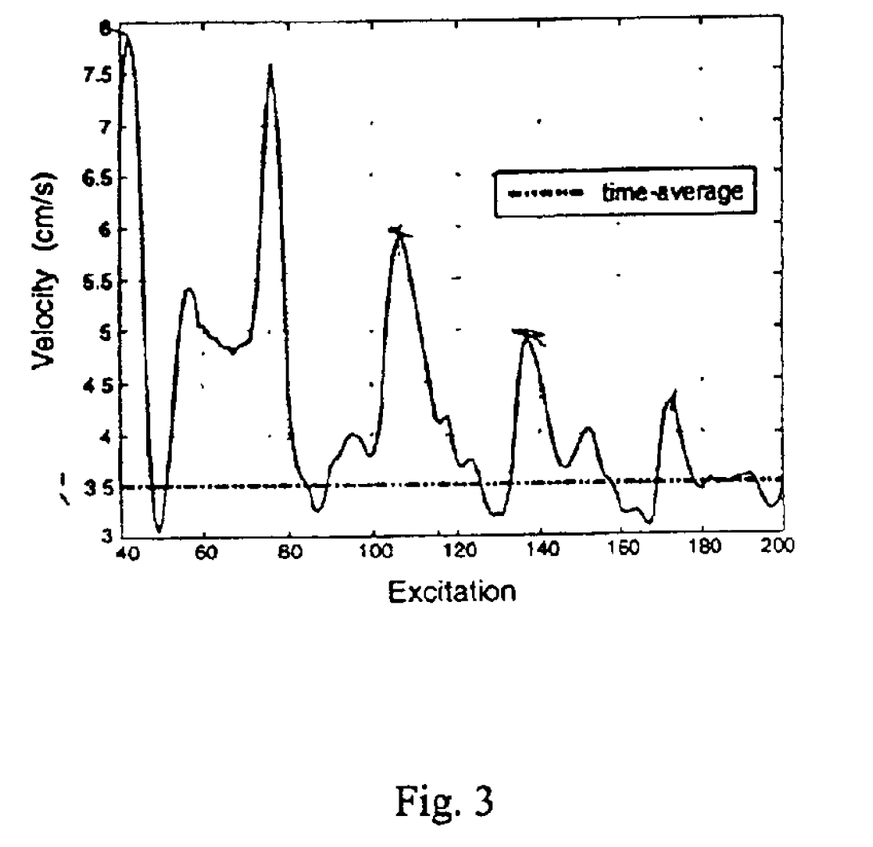
FIG. 3 is a graph illustrating cumulative-average velocity from five continuous scans of ungated spiral phase-contrast data acquisition on the femoral artery of a subject.

This periodic information can be extracted from a graph called a cumulative-average velocity plot, which is reconstructed from the same raw-data sets acquired to measure the time-averaged flow rate. One example of a cumulative-average velocity plot is shown in FIG. 3, which is a cumulative-average velocity plot from the 5 continuous scans of the ungated spiral phase-contrast (USPC) method (with 40 interleave spiral trajectories) on the femoral artery of a normal subject. In this plot, one "excitation" is equivalent to 2TR=30 ms. Each point in a cumulative-average velocity plot is a velocity average acquired by using all the data collected up to that point in time. The procedure for making such a plot can be illustrated by a simplified example: Assume that we want to calculate a cumulative velocity average over 10 excitations from an N=3 spiral PC sequence. For each FE (five excitations, e.g., 1,3,5,7,9), we average the last two excitations (excitations 7 and 9) with the first two excitations (excitations 1 and 3), respectively (we term this "partial averaging"), and then construct an N=3 spiral image. By applying the conventional phase-difference technique, we can calculate a (third) point in the cumulative-average velocity plot. (For an N=3 spiral sequence, we can acquire the first PC image set, the first point in a cumulative-average velocity plot, after six excitations, and we can acquire other PC image sets after every two more excitations.)

The exact cumulative velocity averages are acquired only at the integer multiples of 2N excitations (assuming symmetric temporal velocity distributions) because there is no partial averaging. However, the resulting cumulative-average velocity plot can still be a good approximation to a true cumulative-average velocity (flow) waveform if all we are interested in is the periodic information of a cardiac cycle. Interesting to note here is that a cumulative-average velocity plot eventually approaches the time-averaged velocity over one cardiac cycle, as illustrated in FIG. 3.

From the excitations that cover approximately integer multiples of a cardiac cycle, we can calculate a time-averaged flow rate of interest by using similar post-processing steps in constructing a cumulative-average velocity plot. Before actually quantifying the flow rate, we use conventional methods in the PC technique to correct phase errors and to determine regions of interest (ROIs). We analytically correct the phase errors from the Maxwell terms of the FE lobes, and then correct eddy-current-induced phase-offset errors by linearly fitting the phase of the static regions around a vessel of interest in a phase-difference image. When correcting the eddy-current-induced phase errors, we use only the zeroth-order term in the linear fitting in the cases where static regions were far from the vessel of interest in the prescribed slices, because a small error in the first-order term of a linear phase fit in the static regions will result in significant phase errors at the vessel of interest. Finally we draw an ROI by using a semi-automated program with a threshold.

We validated the USPC method on a pulsatile flow phantom and applied the method to the renal and femoral arteries of normal volunteers. Both studies were performed on a 1.5 T GE Signa whole-body scanner (General Electric, Milwaukee, Wis.) with 40 mT/m gradient amplitude and 150 mT/m/ms slew rate.

Figure 4:
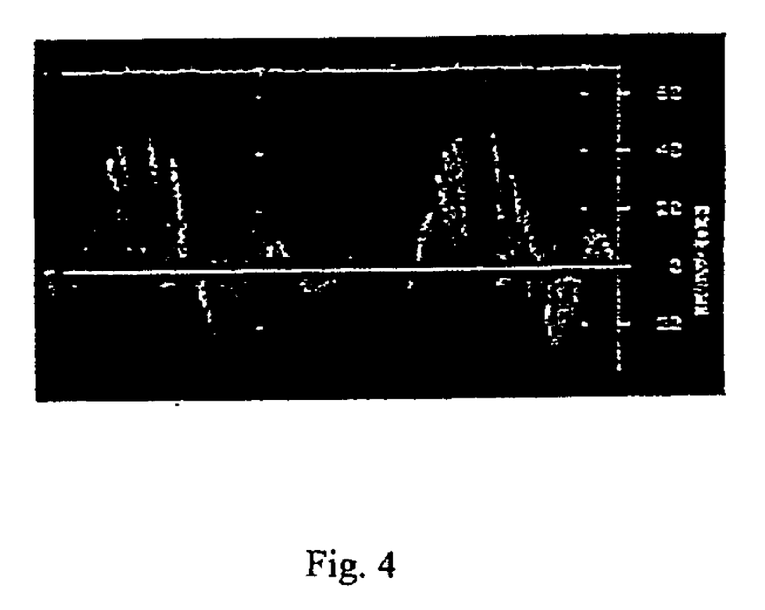
FIG. 4 illustrates a Doppler ultrasound flow waveform showing pulsatility of flow used in experiments.

The flow phantom used with the pulsatile flow pump (Pulsatile Blood Pump, model 1421; Harvard Apparatus, Holliston, Mass.) was made of a rigid plastic box containing water and plastic tubing. The inner and outer diameters of the tubing were 6.2 mm and 8.0 mm, respectively. The pulsatile flow settings of the pump were systole/diastole time ratio=40/60, beats per minute (bpm)=60 and time-averaged flow rates per cycle=3–15 ml/s. FIG. 4 is a velocity/time plot of the pulsatile flow waveform measured using Doppler ultrasound. The velocities in the waveform range between approximately 50 and −25 cm/s.

Figure 5:
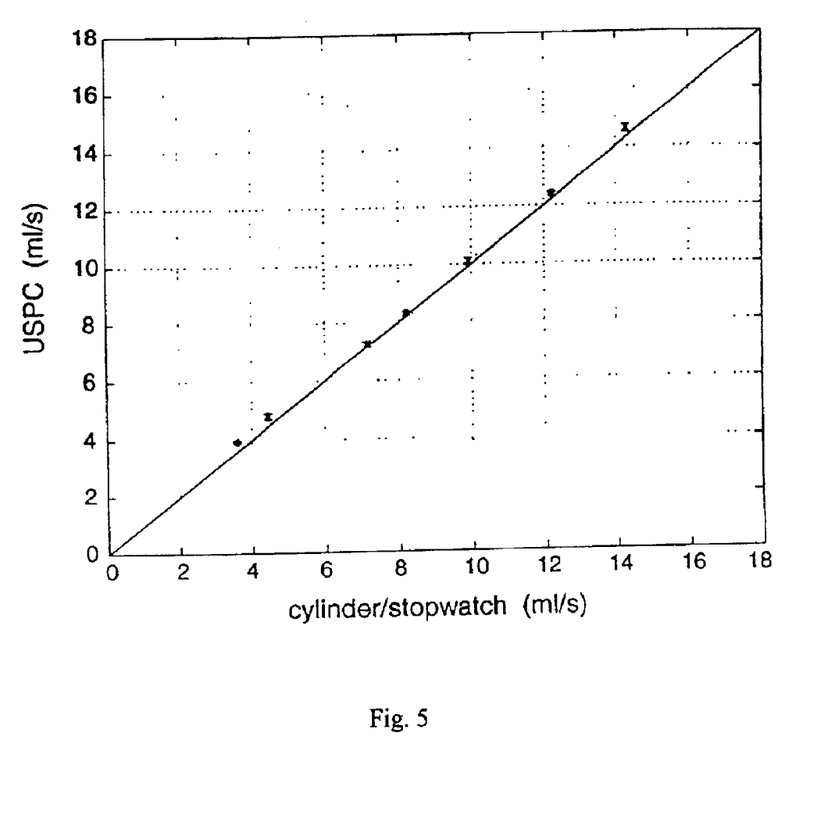
FIG. 5 is a graph illustrating pulsatile flow for a phantom and standard deviations of four repeated measurements with ungated spiral phase contrast.

FIG. 5 shows the time-averaged flow rates measured with the USPC method and a reference (graduated cylinder/stopwatch) method. The vertical and horizontal error bars represent the standard deviations (SDs) of four repeated measurements with the USPC method and the reference method, respectively. The time-averaged flow rates measured with the USPC method (error≦+9%, SD≦2%) agreed well with the reference measurements. The void signal from the tubing most likely caused slight overestimation, as noted in earlier work. The total scan time was six seconds per measurement.

We measured the renal artery blood-flow rates of five normal volunteers with the USPC method. Before applying the USPC method to each individual, we prescribed an oblique axial slice through the target vessel to obtain through-plane flow using a real-time imaging system. The USPC sequence was played out over a brief six-second breath-holding interval.

Figure 6A:
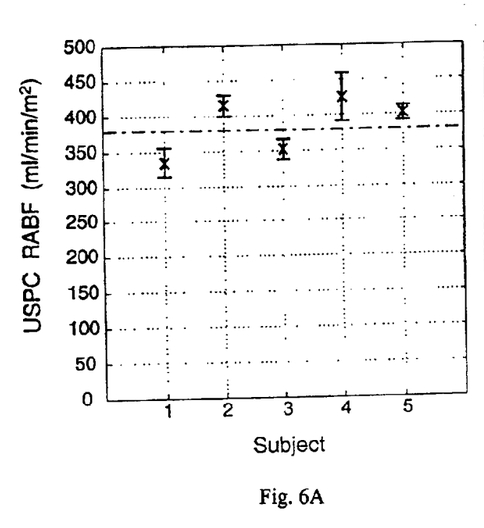
FIGS. 6A, 6B are a graph and an image of right renal artery blood flow rates in five normal volunteers.
Figure 6B:
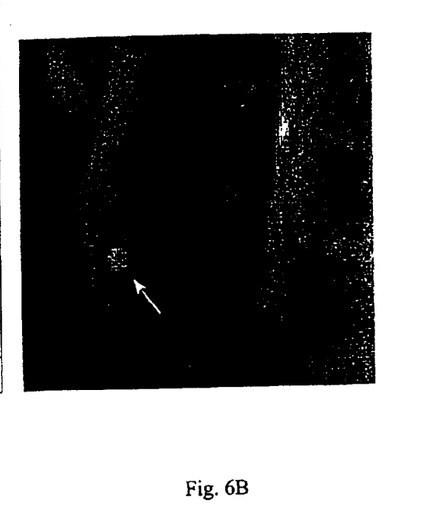

FIGS. 6A, 6B show the time-averaged flow rates in the right renal arteries of five normal volunteers, corrected for their body-surface area (m2). The error bars for each measurement represent the SDs of four USPC measurements for each subject. The results (SD≦8%) agree well with normal renal artery blood-flow rates (380 ml/min/m$^2$ per kidney) known from the literature. The magnitude images showed sharply defined margins of the artery and a homogeneous signal within its lumen, indicating minimal vessel movement and minimal flow artifacts.

Figure 7A:
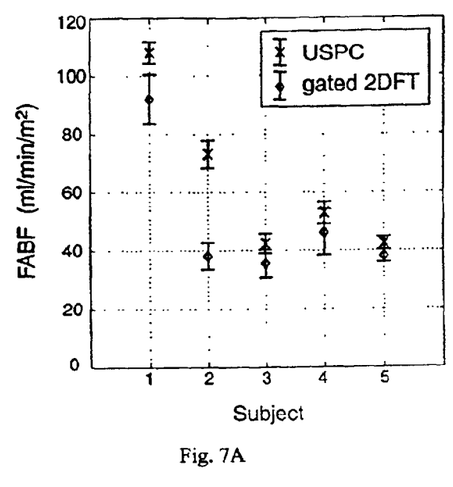
FIGS. 7A, 7B are a graph and an image of femoral artery blood flow rates in five normal volunteers.
Figure 7B:
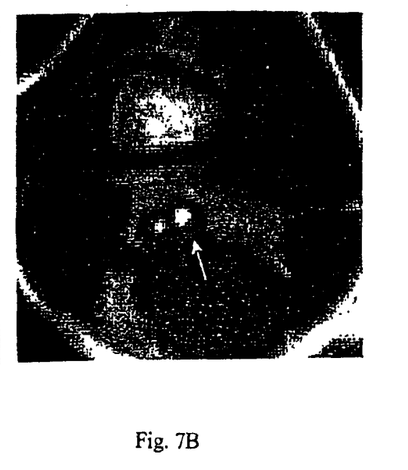

We also applied the USPC method to the femoral arteries of five normal volunteers. FIGS. 7A, 7B show the m$^2$-corrected results. The USPC method was more repeatable than the conventional gated cine-2DFT PC method (FOV/slice/matrix=20 cm/10 mm/256×160, TR/TE/flip angle=20 ms/6 ms/30°, number of frames per cycle=30, VENC=100 cm/s, and total scan time=160 heartbeats), as evidenced by the smaller SDs of the USPC method. Note that we could not apply the gated method to the renal arteries in vivo because of image degradation caused by respiratory motion within the upper abdomen. The error bars represent the standard deviations (SDs) of four repeated measurements for each method. The SDs of the USPC method (SD≦8%) are smaller than those of the conventional gated cine-2DFT PC method (SD≦17%). The magnitude image shows sharply defined margins of the artery (arrow) and a homogeneous signal within its lumen, indicating minimal vessel movement and minimal flow artifacts. Total scan time=6 seconds (USPC) and 2–3.5 minutes (gated 2DFT) for each measurement.

The experimental results show that the USPC method can quickly and repeatedly measure accurate time-averaged blood flow in the presence of strong pulsatility. Even with the strong pulsatility in the flow phantom (see FIG. 4), the USPC method produced accurate (error≦+9%) and repeatable (SD≦2%) measurements of time-averaged flow rates, as shown in FIG. 5. In a very brief breath-hold, the short scan time of the USPC method allowed us to measure time-averaged flow rates in renal arteries, a measurement that is difficult to make with gated methods because of respiratory motion (see FIG. 6). The USPC method was more repeatable than the conventional gated cine-2DFT PC method (see FIG. 7).

The possible sources of measurement errors unique to the USPC method are the asymmetry of and in-flow effects described above, the partial averaging process, and variation in selecting the excitation sets that approximately cover integer multiples of a cardiac cycle. If we consider only the type of asymmetry of the temporal velocity distribution shown in FIG. 2a, we are likely to underestimate the time-averaged velocity because more velocities are below the time-average over one cardiac cycle. If we consider only in-flow effects, we are likely to overestimate the time-averaged velocity due to the RF saturation at low velocities. However, given the sequence parameters used, the asymmetry and in-flow effects we observed were relatively small in all experiments, in agreement with the predictions set forth above. Using more than three cardiac cycles, we were able to minimize the errors in the partial averaging process and the errors introduced by the variation in the selected excitation sets. Note that a trade-off between these errors and scan times exists and that we can minimize most of the errors by using scan times that are longer but still on the order of only a few seconds. FIG. 3, which shows that the cumulative velocity average finally approaches the true time-averaged velocity, makes this intuitively clear. The errors in local phase-offset correction and ROI segmentation, which are inherent in any PC method, were smaller than other possible errors. Vessel displacement during the scan can cause blurring of the vessel in the magnitude image. Although blurring and its accompanying error were minimal in all experiments, we need to investigate further the effects of vessel displacement, especially in areas of particularly vigorous pulsation, where the vessel displacement can be significant over a short period of time (e.g., in the ascending aorta).

Because the phase-difference processing happens after the velocities are temporally averaged in each flow-encoded image, velocity aliasing in the USPC method will not result in ambiguity in the velocity measurement as long as the time-averaged velocity is within ±VENC but may increase the asymmetry and in-flow effect errors. However, the errors from the asymmetry and in-flow effects were still relatively small in our experiments when the peak velocities were greater than the VENC (the last two data points in FIG. 5).

Important advantages of USPC over conventional gated methods include the short scan time and the simplicity of the method. The short scan time provides robustness with respect to irregular heart rhythm and respiratory or other forms of body motion, as illustrated in FIGS. 6 and 7. The simplified imaging protocol of USPC makes this method an efficient tool for measuring time-averaged flow rates in a clinical setting.

Real-time methods can provide alternative ways to quickly measure time-averaged flow rates. Compared to the USPC method, real-time methods acquire complete images more rapidly but cover a relatively smaller portion of k-space. Because of this limited coverage, which results in low spatial resolution, real-time methods are likely to have severe PVEs in small vessels. The USPC method covers more of the k-space but acquires complete images more slowly, and therefore effects other than PVEs (e.g., the asymmetry and in-flow effects, the partial averaging process) may be the larger sources of measurement errors.

The importance of the k-space origin is widely known, and we can use the k-space origin perspective to predict the flow properties of ungated PC techniques with various k-space trajectories such as 2DFT or spiral. In ungated PC techniques, we can intuitively view the process of spatially averaging the velocities over a vessel cross-section as a complex summation of the vessel PSFs because the vessel PSFs interfere with each other and because the average of the phases of all vessel pixels is the phase of the complex sum of the pixels when the spatial velocity distribution is symmetric. Therefore, using the area property of the FT, we can predict that a measured time-averaged flow rate over a vessel cross-section is likely to be biased toward the velocities that were present when the pulse sequence sampled the k-space near the origin. However, the k-space origin perspective alone cannot fully explain why the USPC method works with great accuracy. It is the overall shape of the PSF—the flatness of the phase and the concentration of the magnitude around the center due to the sampling nature of spiral trajectories around the k-space origin (FIG. 2d)—that explains the accuracy and robustness of the USPC method for measuring time-averaged blood-flow rates in the presence of strong pulsatility.

We have shown the potential of the USPC method for rapidly and robustly measuring time-averaged blood flow even in small arteries and in the presence of strong pulsatility. The flow phantom experiment verified that the USPC method can quickly produce accurate measurements of time-averaged flow rates. The USPC method repeatedly produced consistent renal artery blood-flow measurements within a short breath-holding interval. With significantly reduced scan times, the USPC method was more repeatable than the conventional gated cine-2DFT PC method for measuring femoral artery blood-flow rates.

While the invention has been described with reference to specific applications and embodiments, the description is illustrative of the invention and is not to be construed as limiting the invention. For example, variations include extending to 3D imaging, using the method with contrast agents, using a different flow-encoding (FE) scheme with PC, using a different number of interleaves (N) for spiral trajectories, using different sequence parameters (e.g., TR, TE, flip angle, slice thickness, etc.), and using different k-space trajectories which have the similar sampling nature of a spiral trajectory. One can extend the method to 3D flow quantification technique by using FE gradients on all X, Y, and Z gradients. Use of contrast agents can improve SNR in certain imaging areas where high SNR is hard to achieve. The FE scheme described above is a minimum-first-moment FE ($M_f=\pm\Delta M_f/2$). However, other FE methods, such as a standard on-off FE scheme ($M_f=+\Delta M_f$, 0), can be used to achieve different flow properties of the sequence. Different spiral trajectories (i.e., different N) can be used to minimize the possible errors inherent in this method depending on a flow waveform. Similarly, different TR, TE, flip angle, and slice thickness can be used to optimize the sequence for certain object (vessel) and flow of interest. Finally, different k-space trajectories with the similar sampling nature of a spiral trajectory can be used instead of spiral trajectories. Examples of such trajectories are projection reconstruction (PR), twisted radial lines, or variable density spiral trajectories. Thus, various modifications and applications may occur to those skilled in the art without departing from the true scope and spirit of the invention as defined by the appended claims.

What is claimed is:

1. A method of imaging pulsatile blood flow in a patient using magnetic resonance imaging without cardiac gating comprising the steps of:
   a) placing the patient in a static magnetic field,
   b) exciting nuclear spins in the presence of a gradient ($G_z$) for a slice defined by the gradient,
   c) applying a phase contrast flow encoding magnetic pulse following step b), d) applying magnetic read-out gradients ($G_x$, $G_y$) after step c) whereby spiral k-space type sampling is used during read-out, and e) acquiring read-out data, f) repeating steps b)–e) with rotated magnetic readout gradients and without cardiac gating over at least one cardiac cycle, and g) processing the acquired data to obtain time averaged flow rate information.

2. The method as defined by claim 1 wherein the gradient magnetic field ($G_z$) in step b) includes a gradient spoiler.

3. The method as defined by claim 2 wherein the readout gradients in step d) rewind the k-space trajectory to k-space origin.

4. The method as defined by claim 3 wherein step g) includes use of a cumulative-average velocity plot from which a period of a cardiac cycle is obtained.

5. The method as defined by claim 4 wherein step c) applies a flow encoding magnetic pulse having a non-zero first moment.

6. The method as defined by claim 5 wherein in step d) k-space is sampled along spiral k-space trajectories.

7. The method as defined by claim 6 wherein the k-space trajectories are interleaved.

8. The method as defined by claim 7 wherein the k-space trajectories have variable density.

9. The method as defined by claim 5 wherein in step d) k-space sampling is along radial lines.

10. The method as defined by claim 5 wherein in step d) k-space sampling is along twisted radial lines.

11. The method as defined by claim 1 wherein step g) includes use of a cumulative-average velocity plot from which a period of cardiac cycle is obtained.

12. The method as defined by claim 1 wherein step c) applies a flow encoding magnetic pulse having a non-zero first moment.

13. The method as defined by claim 1 wherein in step d) k-space sampling is along spiral k-space trajectories.

14. The method as defined by claim 13 wherein the k-space trajectories are interleaved.

15. The method as defined by claim 14 wherein the k-space trajectories have variable density.

16. The method as defined by claim 1 wherein in step d) k-space sampling is along radial lines.

17. The method as defined by claim 1 wherein in step d) k-space sampling is along twisted radial lines.

18. The method as defined by claim 1 wherein step d) applies three readout gradients ($G_x$, $G_y$, $G_z$) and step g) obtains three dimensional time averaged flow information.

* * * * *